(12) United States Patent
Davis

(10) Patent No.: US 8,951,553 B2
(45) Date of Patent: Feb. 10, 2015

(54) COMPOSITION FOR PROMOTING VASCULAR SMOOTH MUSCLE RELAXATION

(75) Inventor: Adrian Francis Davis, Surrey (GB)

(73) Assignee: Futura Medical Developments Limited Surrey Technology Centre, Guildford, Surrey (GB)

( * ) Notice: Subject to any disclaimer, the term of this patent is extended or adjusted under 35 U.S.C. 154(b) by 1100 days.

(21) Appl. No.: 11/659,815

(22) PCT Filed: Aug. 8, 2005

(86) PCT No.: PCT/GB2005/003110
§ 371 (c)(1),
(2), (4) Date: Feb. 9, 2007

(87) PCT Pub. No.: WO2006/016139
PCT Pub. Date: Feb. 16, 2006

(65) Prior Publication Data
US 2008/0081058 A1  Apr. 3, 2008

(30) Foreign Application Priority Data
Aug. 9, 2004  (GB) .................................. 0417675.6

(51) Int. Cl.
| A61K 9/70 | (2006.01) |
| A61K 9/00 | (2006.01) |
| A61K 31/21 | (2006.01) |
| A61K 47/10 | (2006.01) |

(52) U.S. Cl.
CPC ............. *A61K 9/0034* (2013.01); *A61K 9/0014* (2013.01); *A61K 31/21* (2013.01); *A61K 47/10* (2013.01); *Y10S 514/944* (2013.01)
USPC ......................................... 424/449; 514/944

(58) Field of Classification Search
USPC ........................................................ 424/449
See application file for complete search history.

(56) References Cited

U.S. PATENT DOCUMENTS

| 4,704,119 | A | * | 11/1987 | Shaw et al. .................... 424/448 |
| 5,047,230 | A | | 9/1991 | Nagy et al. |
| 5,370,862 | A | * | 12/1994 | Klokkers-Bethke et al. ... 424/47 |
| 5,744,124 | A | | 4/1998 | Klokkers-Bethke et al. |
| 5,807,569 | A | * | 9/1998 | Davis et al. .................... 424/449 |
| 5,932,227 | A | | 8/1999 | Higo et al. |

FOREIGN PATENT DOCUMENTS

| EP | 0461505 A1 | 12/1991 |
| EP | 0934744 A1 | 8/1999 |
| WO | WO 96/27372 | 9/1996 |

OTHER PUBLICATIONS

NITRO-BID(R) product insert, 2001.*

* cited by examiner

*Primary Examiner* — Paul Zarek
(74) *Attorney, Agent, or Firm* — Clark & Brody

(57) ABSTRACT

A composition for topical application to a part of the body comprises a vasodilator, for example glyceryl trinitrate, as active ingredient dissolved in a blend of volatile and non-volatile solvents of different solvating capacities for the vasodilator. The vasoldator is present in the composition at a concentration at or slightly below saturation, whereby evaporation of the volatile solvent in use will maintain the vasodilator at saturated or super-saturated concentrations in the residue, whereby the vasodilator will become saturated or supersaturated in the solvent remaining and, as the active ingredient passes through the skin and is absorbed in the bloodstream, and thus becomes depleted in the residual composition, continuing evaporation of volatile solvent will maintain the active ingredient substantially at saturation or supersaturation level in the residual composition throughout the major part of the absorption phase, thereby maximising absorption levels but at a moderate dosage level.

12 Claims, 2 Drawing Sheets

COMPOSITION FOR PROMOTING VASCULAR SMOOTH MUSCLE RELAXATION

Figure 1:
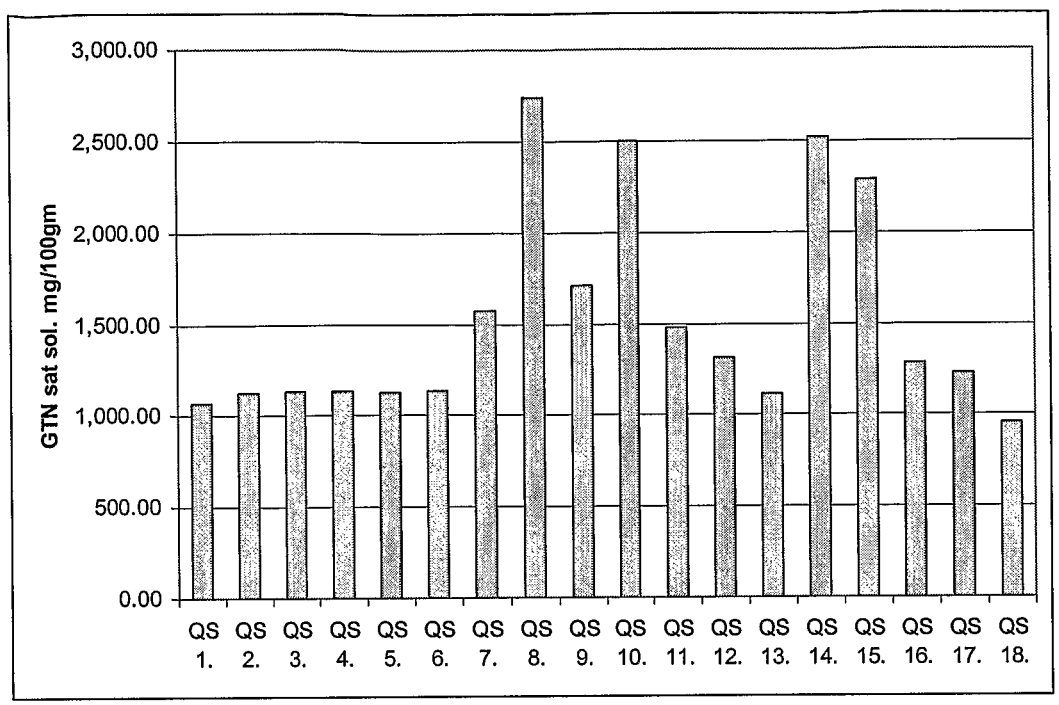

This invention relates to the treatment or amelioration of conditions susceptible to vascular smooth muscle relaxation, especially angina and erectile dysfunction.

Erectile dysfunction—that is, the failure to achieve or sustain an erection of the penis in males sufficient to enable sexual intercourse to take place—is an increasing or increasingly recognised problem. Females also can suffer from erectile dysfunction in that the clitoris does not become sufficiently enlarged during sexual activity to enable optimum sexual satisfaction or fulfilment to be experienced. Angina is experienced when the coronary blood flow is insufficient to meet the heart's metabolic requirements. Both conditions can be treated or ameliorated by the topical application of a vasodilator-containing composition, glyceryl trinitrate or nitroglycerin being a commonly-used vasodilator for this purpose.

For treatment of erectile dysfunction, the glyceryl trinitrate (GTN) or other vasodilator, on application to erectile genitalia and absorption through the skin, results in a local enhancement in blood supply to the organ and hence to a better quality of erection. One such composition is described in WO 99/38506 and contains lanolin as a lubricant and as a skin penetration enhancement material. It has been found that such compositions result in use in a surprisingly low incidence of headache (a known side effect of GTN when used, for example, for the treatment of angina). However, although such compositions may be effective, significant absorption of GTN into the blood stream may occur resulting in systemic adverse effects and the potential for drug interactions.

A further composition, especially for use in the treatment of angina, is described in U.S. Pat. No. 5,047,230 as an aerosol composition containing no propellant gas and comprising GTN as active ingredient dispersed in 51-90% by weight of a $C_{2-4}$ aliphatic alcohol, preferably ethanol, 10-49% by weight of a polyalkyleneglycol having 2 or 3 carbon atoms in the alkylene moiety, and/or a $C_{2-8}$ alcohol having two or three hydroxyl groups. The high alcohol concentration results by virtue of exerting a direct effect on the skin barrier, in better and faster absorption of the active ingredient. However, for application to the male or female genitalia, such high alcohol concentrations cause a burning or stinging sensation and are therefore unacceptable.

Ideally, for treatment of erectile dysfunction in males, targeted delivery to the penis is required whereby local, regional, effects of the drug are enjoyed but such that systemic distribution and subsequent systemic effects are avoided. Although such an ideal solution is unachievable in practice because at least some systemic uptake is inevitable following topical administration, use of low doses of GTN delivered as a "virtual injection" would approximate to the ideal state, provided that transdermal or percutaneous absorption was sufficiently rapid. Once tumescence and erection is achieved by pharmacological intervention, physiological block of the venous return of blood will self sustain the erection. The requirements to provide a composition from which sufficient active ingredient will be absorbed for initiating the intended effect, while maintaining the dose at a low level to avoid subsequent systemic effects, are thus to some extent mutually conflicting.

Many technologies have been described to increase percutaneous penetration. Amongst these it is well known to saturate the drug in the formulation so as to optimise partitioning into and thus solubility in the stratum corneum barrier of the skin and thus also to optimise percutaneous transport. For the vast majority of drugs, this results in zero-order steady-state maximum input into the skin over the dosing period. In part this zero order is due to the extent of absorption being so low, compared to the dose applied, that no effective depletion of the saturated, optimum, state occurs. However, with drugs that are efficiently absorbed and especially when the drug is applied at a low dose, as in the case of a "virtual injection" as described above, rapid depletion significantly reduces the degree of saturation, the chemical activity state, of the active ingredient in the formulation and thus reduces the transport rate.

It is therefore an object of the present invention to provide a composition which, on being applied to the skin, maintains the degree of saturation and the chemical activity state of active ingredient therein essentially throughout the absorption process to provide a continuing driving force as percutaneous absorption takes place. It is also an object to provide a composition which, while providing for continuing percutaneous absorption of active ingredient, also provides a low half-life of active ingredient in the bloodstream, thus resulting in rapid elimination so as not to accumulate in the systemic circulation.

In one aspect, the invention provides a composition for topical application to a part of the body, the composition comprising a vasodilator as active ingredient dissolved in a blend of volatile and non-volatile solvents of different solvating capacities for the vasodilator.

The vasolidator is present in the composition as formulated at a concentration at or slightly below saturation, whereby evaporation of the volatile solvent in use will maintain the vasodilator at saturated or super-saturated concentrations in the residue.

Preferably, the non-volatile solvent has the lower solvating capacity, compared with the volatile solvent.

The vasodilator preferably comprises glyceryl trinitrate.

In use and on application to an affected body part such as erectile tissue, for example the penis, by hand, the composition will form a thin film over the glans and along and around the penile shaft, thereby providing an extended surface area over which the composition is supported and which, in combination with body warmth, will cause the volatile solvent component to evaporate. The glyceryl trinitrate or other vasodilator will thus become saturated or supersaturated in the solvent remaining and, as the active ingredient passes through the skin and is absorbed in the bloodstream, and thus becomes depleted in the residual composition, continuing evaporation of volatile solvent will maintain the active ingredient substantially at saturation or supersaturation level in the residual composition throughout the major part of the absorption phase, thereby maximising absorption levels but at a moderate dosage level.

In another aspect, therefore, the invention provides a method for the treatment or amelioration of a condition susceptible to vascular smooth muscle relaxation, the method comprising topical application to an affected body part of a composition comprising a vasodilator as active ingredient dissolved in a blend of volatile and non-volatile solvents of different solvating capacities for the vasodilator, and allowing volatile solvent to evaporate.

Compositions according to the invention may be supplied in a tube or other container but preferably are provided in unit-dosage form or applied to a condom. In unit-dosage form or as applied to a condom, the dose of vasodilator should be up to 5 mg, preferably 2.5 mg or less, for example 1.0 mg or even 0.5 mg. Thus, for a nominal concentration of vasodilator of 1.0% by weight in the composition as formulated, a unit dose of 100 mg would provide 1.0 mg of vasodilator.

In compositions according to the invention, the solvents are water-miscible and the consistency is preferably that of a spreadable gel or a cream. For reasons of aesthetic consumer acceptability, the gel is preferably relatively clear and colourless and has an agreeable feel on the skin, without being gloopy or leaving gloopy residues as absorption proceeds. Preferably and since the composition may be supplied as a coating or layer to a condom, the solvents should not interreact with or degrade condom materials.

The volatile solvent component in compositions according to the invention preferably comprises a mixture of water with a low molecular weight alcohol to enhance the solvating power and to lower the boiling point. A suitable alcohol comprises ethanol, for reasons of cost, availability, volatility and toxicity, but other lower alcohols containing up to five carbon atoms may be used, preferably isopropanol, as an alternative or additionally to ethanol. The water and volatile solvent may be present in a ratio from 0.5:1 to 1.6:1, preferably 0.7:1 to 1.5:1, by weight. For example, using ethanol as the volatile solvent, the percentages by weight may be 40% water, 30% ethanol (1.3:1) or 29% water, 36% ethanol (0.8:1), the balance in each case being non-volatile solvent. In a more preferred range, the ratio would be 1:1 or higher. The alcohol preferably has a maximum concentration of 40% by weight, more preferably 35% or even 30% by weight, based on the total formulation. In compositions according to the invention, it has been found that percutaneous absorption is rapid despite a low alcohol concentration, because of the effect of the solvent blend in maintaining the active ingredient concentration at saturation or supersaturation levels in the residual composition as absorption takes place.

The non-volatile solvent, which preferably has the lower solvating capacity, is present preferably in a lower concentration than the volatile solvent, preferably 40% by weight or lower of the total solvent content, preferably less than 35% or even less than 30%, to enhance the skin properties. The non-volatile solvent may comprise a polyhydric alcohol, glycerol (boiling point 290° C.) being preferred for reasons of availability and acceptability. The high-boiling alcohol may be blended with a minor amount of additional solvent to modify its properties. A suitable additional solvent comprises a glycol, for example propylene glycol, which may be present at up to 20% of the total non-volatile component, preferably up to 15%, for example 5.0% by weight or 12.5% by weight.

In general, it has been found that high levels of supersaturation in the residual phase after evaporation of volatile solvents in use may be generated by selecting the solvents so as to provide a volatile solvent component allowing a saturated solubility of glyceryl trinitrate in excess of 1% with a non-volatile solvent component allowing a saturated solubility of less than 1%. However, within this requirement, it is desirable that the maximum concentration of ethanol (as the volatile co-solvent with water) should not exceed 40% of the total solvent component and that the maximum concentration of glycerol (as the primary non-volatile solvent) should not exceed 30%, although in each case these limits are not absolute and are based on anticipated user acceptance levels. In compositions according to the invention as supplied for use, glyceryl trinitrate as the vasodilator is preferably present in the total solvent system at a slightly sub-saturated concentration to allow super-saturation to occur upon loss of volatile components.

Compositions according to the invention also optionally include additional ingredients such as agents for enhancing skin feel, for example a silicone oil composition such as Dimethicone 200; thickening or gelling agents, for example a polyacrylate-based composition such as Carbopol 937P; neutralising agents such as triethanolamine; and antimicrobial preservatives such as Propylparaben.

It has been found that, based on an in vitro experimental model using a SAMCO silastic membrane to simulate skin, compositions according to the invention exhibit improved trans-dermal transport properties compared with Percutol, an available topical composition containing glyceryl trinitrate for the treatment of angina.

Figure 2:
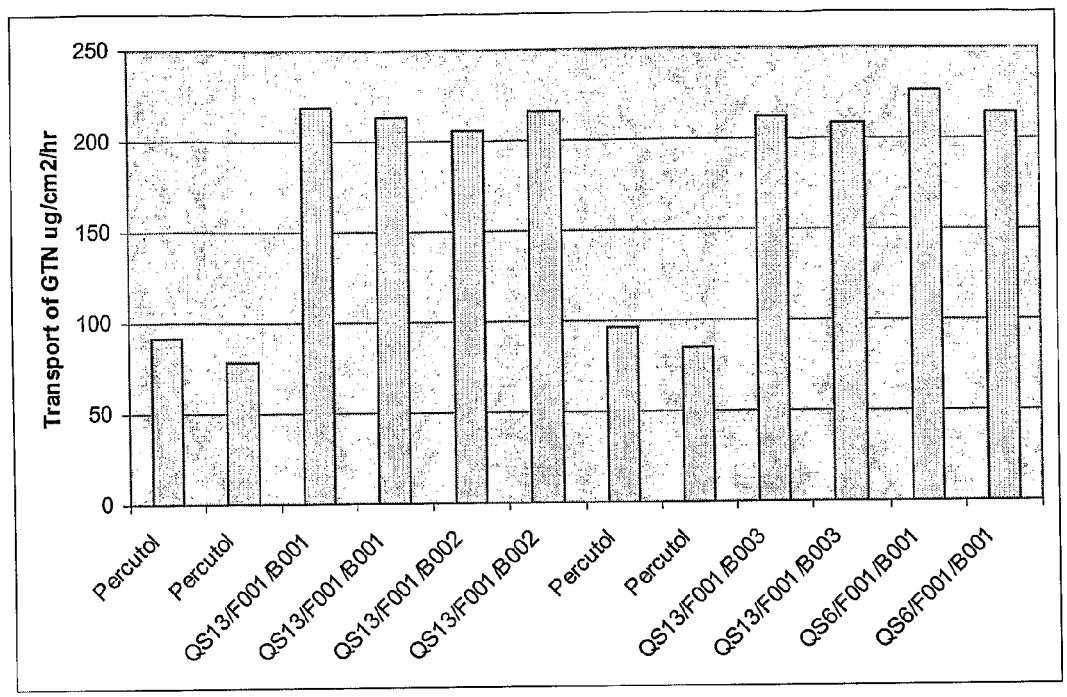

The invention will now be described with reference to the following experimental details, provided purely by way of example, and with reference to the accompanying drawings, of which:

FIG. 1 is a bargraph showing comparative saturated solubility of GTN in various solvent blends; and FIG. 2 is a bargraph showing in vitro transport of compositions according to the invention compared with Percutol.

The experiments provided compositions having a nominal concentration of glyceryl trinitrate of a minimum of 1% or 2% based on the total of volatile and non-volatile solvents. The solvents used were water and ethanol as the volatile component and glycerol together with propylene glycol as an optional additive as the non-volatile component. The experiments related to the use of three respective variables, firstly various ratios of 1% glyceryl trinitrate (GTN) in 57.5:42.5 water:ethanol (1.35:1) and 1% GTN in 87.5:12.5 glycerol:propylene glycol (7:1) (QS 1-QS 6); secondly GTN in various ratios of water-ethanol systems and GTN in glycerol alone (QS 7-QS 13); and thirdly GTN in various ratios of different water:ethanol systems with GTN in 95:5 glycerol:propylene glycol (QS 14-QS 18). For each experiment, the concentration of GTN remaining in the residual (non-volatile) solvent and expressed as a multiple of the saturated concentration was estimated, based on volume change and taking account of the saturated concentration in the solvent or solvent blend of the residual phase.

Initially, predicted saturated concentration in the quarternary solvent blends was estimated based on experimental determinations in binary cosolvents, namely ethanol/water at different ratios and glycerol/propylene glycol at different ratios. It was predicted that the saturated concentration of GTN would be 1% in most quaternary blends or 2% in others (QS 8, QS 10, QS 14 and QS 15). FIG. 1 shows experimental data for the saturated solubility of GTN in the various quaternary and tertiary (QS 7-QS 13) blends. As illustrated, good agreement with prediction was shown by QS 1 to QS 6; QS 7 to QS 13 showed higher solubilities than predicted and QS 14 to QS 18 were also higher, albeit not to the same extent as with QS 7 to QS 13.

Table 1 shows the details of each experiment and the estimated residual concentration of GTN expressed as a multiple of the saturated concentration in the residual solvent.

TABLE 1

| Series (W-E:G-PG) | Water (%) | Ethanol (%) | Glycerol (%) | Prop Glycol (%) | Conc. Of GTN (predicted) (%), Approx. *SS (predicted) |
|---|---|---|---|---|---|
| QS 1. | 28.75 | 21.25 | 43.75 | 6.25 | (1), *2 |
| QS 2. | 31.65 | 23.375 | 39.375 | 5.625 | (1), *2.2 |
| QS 3. | 34.5 | 25.5 | 35.5 | 5.0 | (1), *2.5 |
| QS 4. | 37.375 | 27.625 | 30.625 | 4.375 | (1), *2.86 |

TABLE 1-continued

| Series (W-E:G-PG) | Water (%) | Ethanol (%) | Glycerol (%) | Prop Glycol (%) | Conc. Of GTN (predicted) (%), Approx. *SS (predicted) |
|---|---|---|---|---|---|
| QS 5. | 40.25 | 29.75 | 26.25 | 3.75 | (1), *3.33 |
| QS 6. | 43.125 | 31.875 | 21.875 | 3.125 | (1), *4 |
| QS 7. | 15.2 | 22.8 | 62 | 0 | (1), *4.24 |
| QS 8. | 25.6 | 38.4 | 36.0 | 0 | (2), *14.61 |
| QS 9. | 19.8 | 24.2 | 56.0 | 0 | (1), *4.70 |
| QS 10. | 33.3 | 40.7 | 26 | 0 | (2), *20.23 |
| QS 11. | 27.0 | 27.0 | 46 | 0 | (1), *5.72 |
| QS 12. | 42.9 | 35.1 | 22 | 0 | (1), *11.94 |
| QS 13. | 39.55 | 30.45 | 30 | 0 | (1), *8.76 |
| QS 14. | 21.6 | 32.4 | 43.7 | 2.3 | (2), *5.35 |
| QS 15. | 29.25 | 35.75 | 33.25 | 1.75 | (2), *7.03 |
| QS 16. | 15. | 15. | 66.50 | 3.50 | (1), *1.76 |
| QS 17. | 30.25 | 24.75 | 41.75 | 2.25 | (1), *2.77 |
| QS 18. | 41.125 | 28.875 | 28.5 | 1.5 | (1), *4.1 |

Note that QS 8, 10, 14 and 15 had a predicted 2% GTN concentration whereas the remainder had a 1% concentration.

From the above results, it is seen that QS 4, QS 5, QS 6, QS 12, QS 13, QS 15 and QS 18 provide promising results in terms of supersaturation in the residual solvent and are within the requirements for ethanol and glycerol limits, respectively. QS 3, QS 8 and QS 10 are also identified as of interest, although QS 10 has a concentration of ethanol which is higher than considered desirable. The remainder, although showing enhanced levels of supersaturation in the residual solvent, may be unacceptable because of the glycerol levels.

The following Table 2 shows the formulation of compositions using solvent blends QS 6 and QS 13, in percentages by weight.

TABLE 2

| Ingredient | QS 6. | QS 13. |
|---|---|---|
| GTN (10% on lactose) | 10 | 10 |
| Water | 38.25 | 35.08 |
| Ethanol | 28.97 | 27.01 |
| Glycerol | 19.41 | 26.61 |
| Propyleneplycol | 2.77 | — |
| Dimethicone 200 | — | — |
| Carbopol 937P | 1.00 | 1.00 |
| Triethanolamine | 0.20 | 0.20 |
| Propylparaben | 0.10 | 0.10 |

To evaluate skin absorption, the experimental systems QS 6 and QS 13 were compared with Percutol in an experimental model in which diffusion of GTN from the test solvent through a SAMCO Silastic membrane into a buffered phosphate receptor fluid was assessed over a period of one hour. All experimental systems performed appreciably (between twice and three times) better than Percutol as shown in accompanying FIG. 2.

However, such in vitro tests, which are difficult to conduct under finite dose, thin-film conditions, may not be fully predictive of in vitro performance. Thus, compositions according to the present invention have also been evaluated in a Phase 1 clinical trial in comparison with a formulation according to WO99/38506. Results are presented in the following Table 3 for peak systemic levels ($C_{max}$), time taken to achieve peak systemic levels ($T_{max}$) and plasma half-life ($t_{1/2}$).

TABLE 3

| Formulation | GTN dose (mg) | $C_{max}$ (pg/ml) | $T_{max}$ (minutes) | $t_{1/2}$ (minutes) |
|---|---|---|---|---|
| WO99/38506 | 20.0 | 949.64 | 25.94 | 96.31 |
| Current | 1.0 | 1267.50 | 14.67 | 8.53 |

As can be seen, peak systemic levels for the current formulation, at a dose of 1 mg, are significantly higher than for the lanolin-containing composition at a dose of 20 mg. The shorter time taken to achieve the peak systemic levels is indicative of more rapid GTN absorption, despite the lower dose. The significantly shorter half-life indicates rapid absorption and rapid elimination of GTN. The current formulation is estimated to be approximately 25-fold more effective than the lanolin-containing formulation at delivery through the membrane of the glans penis.

The invention claimed is:

1. A spreadable gel or cream for topical application to a part of the body comprising a vasodilator as active ingredient dissolved in a blend of volatile and non-volatile solvents of different solvating capacities for the vasodilator, wherein the volatile solvent comprises a mixture of water with a $C_1$ to $C_5$ alcohol and the non-volatile solvent comprises glycerol, with an optional solvent comprising a glycol, the glycerol amount ranging from 22 to 40% by weight based on the total solvent content, wherein the alcohol has a maximum concentration of 40% by weight based on the total solvent content, and further wherein the water and alcohol are present in a ratio from 0.5:1 to 1.6:1 by weight and a concentration of the vasodilator is at or slightly below saturation.

2. A composition according to claim 1, in which the non-volatile solvent has the lower solvating capacity.

3. A composition according to claim 1, in which the vasodilator comprises glyceryl trinitrate.

4. A composition according to claim 1 in unit-dosage form and containing a dose of vasodilator up to 5 mg.

5. A composition according to claim 1, in which the alcohol comprises ethanol.

6. A composition according to claim 1, in which the glycol comprises propylene glycol and is present at up to 20% of the total non-volatile component.

7. A method of preparing a composition for topical application to a part of a body for treatment of a condition susceptible to vascular smooth muscle relaxation comprising combining a vasodilator and a blend of volatile and non-volatile solvents of different solvating capacities to form the composition for topical application as a spreadable gel or a cream to a part of the body for treatment of a condition susceptible to vascular smooth muscle relaxation, wherein the volatile solvent comprises a mixture of water with a $C_1$ to $C_5$ alcohol and the non-volatile solvent comprises glycerol, with an optional solvent comprising a glycol, the glycerol amount ranging from 22 to 40% by weight based on the total solvent content, wherein the alcohol has a maximum concentration of 40% by weight based on the total solvent content, and further wherein the water and alcohol are present in a ratio from 0.5:1 to 1.6:1 by weight and a concentration of the vasodilator is at or slightly below saturation.

8. A spreadable gel or a cream and a vasodilator as active ingredient dissolved in a blend of volatile and non-volatile solvents of different solvating capacities for the vasodilator, wherein the volatile solvent comprises a mixture of water with a $C_1$ to $C_5$ alcohol and the non-volatile solvent comprises glycerol, with an optional solvent comprising a glycol, the glycerol amount ranging from 22 to 40% by weight based on the total solvent content, the composition for use in a method for the treatment or amelioration of angina or erectile dysfunction, wherein the alcohol has a maximum concentration of 40% by weight based on the total solvent content, and further wherein the water and alcohol are present in a ratio from 0.5:1 to 1.6:1 by weight and a concentration of the vasodilator is at or slightly below saturation.

9. The method of claim 7, wherein the vasodilator as the active ingredient and the volatile and non-volatile solvents of different solvating capacities for the vasodilator are included together in the spreadable gel or cream.

10. A container, a unit dosage form, or a condom containing the spreadable gel or cream of claim 1.

11. The method of claim 9, wherein the spreadable gel or cream is in a container or in unit dosage form.

12. A container, a unit dosage form, or a condom containing the spreadable gel or cream and vasodilator of claim 8.

* * * * *